(12) United States Patent
Wang et al.

(10) Patent No.: US 10,288,655 B2
(45) Date of Patent: May 14, 2019

(54) TOUCH STRUCTURE, TEST METHOD THEREOF, TOUCH PANEL AND DISPLAY APPARATUS

(71) Applicants: BOE TECHNOLOGY GROUP CO., LTD., Beijing (CN); HEFEI XINSHENG OPTOELECTRONICS TECHNOLOGY CO., LTD., Hefei, Anhui (CN)

(72) Inventors: Zhun Wang, Beijing (CN); Bisheng Li, Beijing (CN); Zhenzhong Fang, Beijing (CN); Xiaoyue He, Beijing (CN); Wenjin Fan, Beijing (CN)

(73) Assignees: BOE TECHNOLOGY GROUP CO., LTD., Beijing (CN); HEFEI XINSHENG OPTOELECTRONICS TECHNOLOGY CO., LTD., Hefei, Anhui (CN)

( * ) Notice: Subject to any disclaimer, the term of this patent is extended or adjusted under 35 U.S.C. 154(b) by 0 days.

(21) Appl. No.: 15/745,134

(22) PCT Filed: Jul. 7, 2017

(86) PCT No.: PCT/CN2017/092200
§ 371 (c)(1),
(2) Date: Jan. 15, 2018

(87) PCT Pub. No.: WO2018/045814
PCT Pub. Date: Mar. 15, 2018

(65) Prior Publication Data
US 2019/0018050 A1    Jan. 17, 2019

(30) Foreign Application Priority Data

Sep. 12, 2016   (CN) .......................... 2016 1 0819343

(51) Int. Cl.
*G01R 27/14* (2006.01)
*G06F 3/045* (2006.01)
(Continued)

(52) U.S. Cl.
CPC ............. *G01R 27/14* (2013.01); *G01N 27/04* (2013.01); *G01R 27/00* (2013.01); *G01R 31/00* (2013.01);
(Continued)

(58) Field of Classification Search
None
See application file for complete search history.

(56) References Cited

U.S. PATENT DOCUMENTS 9,778,514 B2 * 10/2017 Lv ........................ G02F 1/13394
10,120,516 B2 * 11/2018 Wang ...................... G06F 3/044
(Continued)

FOREIGN PATENT DOCUMENTS

| CN | 203444049 U | 2/2014 |
|---|---|---|
| CN | 103941109 A | 7/2014 |

(Continued)

OTHER PUBLICATIONS

International Search Report and Box V of Written Opinion, for PCT Patent Application No. PCT/CN2017/092200, dated Sep. 30, 2017, 10 pages.

*Primary Examiner* — Jermele M Hollington
(74) *Attorney, Agent, or Firm* — Kinney & Lange, P.A.

(57) ABSTRACT

The present disclosure provides a touch structure, a test method thereof, a touch panel and a display apparatus. In the touch structure, by taking touch driving electrodes as an example, a plurality of third leads which are insulated from each other and are in one-to-one correspondence with various touch driving electrodes are additionally provided, wherein each of the third leads has one terminal electrically (Continued)

connected to a corresponding touch driving electrode and the other terminal serving as a test point for testing whether there is an open circuit on the corresponding touch driving electrode and the corresponding first lead. In this way, two probes may be placed at a test point in a third lead and a first wiring terminal in a binding area respectively when an open circuit test is conducted on each of the touch driving electrodes and a corresponding first lead.

20 Claims, 5 Drawing Sheets

(51) Int. Cl.
    *G01R 27/00*    (2006.01)
    *G01R 31/00*    (2006.01)
    *G01R 31/02*    (2006.01)
    *G01N 27/04*    (2006.01)
    *G01R 31/28*    (2006.01)

(52) U.S. Cl.
    CPC ......... *G01R 31/02* (2013.01); *G01R 31/2812* (2013.01); *G06F 3/045* (2013.01)

(56) References Cited

U.S. PATENT DOCUMENTS

| | | | |
|---|---|---|---|
| 2014/0043038 | A1 | 2/2014 | Chen et al. |
| 2018/0373367 | A1* | 12/2018 | Wang ..................... G06F 3/041 |
| 2019/0004645 | A1* | 1/2019 | Wang ..................... G06F 3/041 |

FOREIGN PATENT DOCUMENTS

| | | |
|---|---|---|
| CN | 103969538 A | 8/2014 |
| CN | 104678186 A | 6/2015 |
| CN | 106370967 A | 2/2017 |
| JP | 2004093268 A | 3/2004 |

* cited by examiner

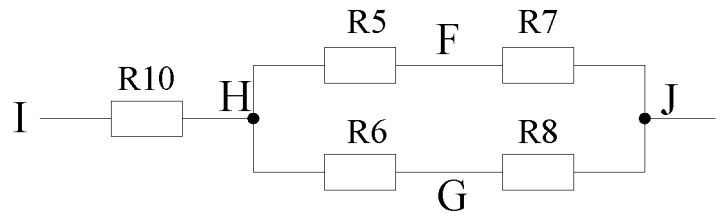

Fig. 5

Fig. 6

```
┌─────────────────────────────────────────┐
│   measuring, for each touch driving      │         S701
│ electrode, a resistance between a test   │
│ point for the touch driving electrode    │
│ and a first wiring terminal to determine │
│ whether there is an open circuit on the  │
│ touch driving electrode and a            │
│ corresponding first lead                 │
└─────────────────────────────────────────┘
                    │
                    ▼
┌─────────────────────────────────────────┐
│   measuring, for each touch sensing      │         S702
│ electrode, a resistance between a test   │
│ point for the touch sensing electrode    │
│ and a second wiring terminal to determine│
│ whether there is an open circuit on the  │
│ touch sensing electrode and a            │
│ corresponding second lead                │
└─────────────────────────────────────────┘
```

Fig. 7

TOUCH STRUCTURE, TEST METHOD THEREOF, TOUCH PANEL AND DISPLAY APPARATUS

CROSS-REFERENCE TO RELATED APPLICATION(S)

This application is the national phase of PCT Application No. PCT/CN2017/092200, which in turn claims priority to the Chinese Patent Application No. 201610819343.X, filed on Sep. 12, 2016, which is incorporated herein by reference in its entirety.

TECHNICAL FIELD

The present disclosure relates to the field of display technology, and more particularly, to a touch structure, a test method thereof, a touch panel and a display apparatus.

BACKGROUND

Touch panels may be divided into add on mode touch panels, on cell touch panels and in cell touch panels in accordance with composition structures thereof. In addition, touch panels may be divided into resistive touch panels and capacitive touch panels and the like in accordance with working principles.

In a conventional touch panel, there are mainly three types of connection manners between a touch electrode and leads. In the first type of connection manner, two leads are drawn from two terminals of the touch electrode, respectively, and the two leads are electrically connected to two wiring terminals in a binding area, respectively. In the second type of connection manner, two leads are drawn from two terminals of the touch electrode, respectively, and the two leads are electrically connected to a same wiring terminal in a binding area, that is, the touch electrode and the two leads form a closed loop structure. In the third type of connection manner, a lead is drawn from one terminal of the touch electrode, and the lead is electrically connected to a wiring terminal in a binding area.

In a process of manufacturing the touch panel, after the touch electrode and the leads are formed, it is required to test whether there is an open circuit on the touch electrode and the leads to ensure the yield rate of the touch panel. When an open circuit test is conducted on the touch electrode and the leads in the first type of connection structure, two probes may be placed at the two wiring terminals in the binding area, and a resistance between the two probes is tested to determine whether there is an open circuit on the touch electrode and the leads. The open circuit test on the touch electrode and the leads in the first structure will not be affected regardless of whether an insulating layer is laid on the touch electrode. When an open circuit test is conducted on the touch electrode and the lead(s) in the second type of connection structure and the third type of connection structure, two probes are required to be placed at the touch electrode and the wiring terminal in the binding area, respectively, and a resistance between the two probes is tested to determine whether there is an open circuit on the touch electrode and the lead(s). If an insulating layer is laid on the touch electrode, the probes cannot be electrically connected to the touch electrode, that is, it is not operable to conduct the open circuit tests on the touch electrode and the lead(s) in the second type of connection structure and the third type of connection structure.

SUMMARY

In view of this, the embodiments of the present disclosure provide a touch structure, a test method thereof, a touch panel and a display apparatus, so as to be capable of performing an open circuit test on any touch structure.

Therefore, the embodiments of the present disclosure provide a touch structure. The touch structure comprises: a plurality of touch driving electrodes; a plurality of touch sensing electrodes provided to intersect with the plurality of touch driving electrodes in an insulating manner; a plurality of first leads insulated from each other and electrically connected to the touch driving electrodes in one-to-one correspondence; a plurality of second leads insulated from each other and electrically connected to the touch sensing electrodes in one-to-one correspondence; a plurality of third leads insulated from each other and in one-to-one correspondence with the touch driving electrodes, wherein each third lead has one terminal electrically connected to a corresponding touch driving electrode and the other terminal serving as a test point for the touch driving electrode for testing whether there is an open circuit on the corresponding touch driving electrode and a corresponding first lead; and/or a plurality of fourth leads which are insulated from each other and are in one-to-one correspondence with the touch sensing electrodes, wherein each fourth lead has one terminal electrically connected to a corresponding touch sensing electrode and the other terminal serving as a test point for the touch sensing electrode for testing whether there is an open circuit on the corresponding touch sensing electrode and a corresponding second lead.

In a possible implementation, in the touch structure according to the embodiments of the present disclosure, the third leads are provided in a same layer as the touch driving electrodes; and a third lead corresponding to one of touch driving electrodes different from two outermost touch driving electrodes is located in a gap between the corresponding touch driving electrode and an adjacent touch driving electrode, and a third lead corresponding to one of the two outermost touch driving electrodes is located in a gap between the corresponding touch driving electrode and an adjacent touch driving electrode or is located on one side of the touch driving electrode away from the adjacent touch driving electrode. The fourth leads are provided in a same layer as the touch sensing electrodes; and a fourth lead corresponding to one of touch sensing electrodes different from two outermost touch sensing electrodes is located in a gap between the corresponding touch sensing electrode and an adjacent touch sensing electrode; or a fourth lead corresponding to one of the two outermost touch sensing electrodes is located in a gap between the corresponding touch sensing electrode and an adjacent touch sensing electrode or is located on one side of the touch sensing electrode away from the adjacent touch sensing electrode.

In a possible implementation, in the touch structure according to the embodiments of the present disclosure, each first lead comprises a first sub-lead and a second sub-lead, wherein each touch driving electrode has one terminal electrically connected to one terminal of a first sub-lead of a corresponding first lead, and the other terminal electrically connected to one terminal of a second sub-lead of the corresponding first lead, the other terminal of the first sub-lead is electrically connected to the other terminal of the second sub-lead, and both the other terminal of the first sub-lead and the other terminal of the second sub-lead are electrically connected to a first wiring terminal in a binding area. Each second lead comprises a third sub-lead and a fourth sub-lead, wherein each touch sensing electrode has one terminal electrically connected to one terminal of a third sub-lead of a corresponding second lead, and the other terminal electrically connected to one terminal of a fourth sub-lead of the corresponding second lead, the other terminal of the third sub-lead is electrically connected to the other terminal of the fourth sub-lead, and both the other terminal of the third sub-lead and the other terminal of the fourth sub-lead are electrically connected to a second wiring terminal in the binding area.

In a possible implementation, in the touch structure according to the embodiments of the present disclosure, a resistance of a part of the touch driving electrode between a position where the touch driving electrode is electrically connected to the corresponding third lead and a position where the touch driving electrode is electrically connected to the first sub-lead is R1, a resistance of a part of the touch driving electrode between a position where the touch driving electrode is electrically connected to the corresponding third lead and a position where the touch driving electrode is electrically connected to the second sub-lead is R2, a resistance of the first sub-lead is R3, a resistance of the second sub-lead is R4, and R1, R2, R3 and R4 satisfy $$2 \leq \frac{R1+R3}{R2+R4} \leq 9 \text{ or } 2 \leq \frac{R2+R4}{R1+R3} \leq 9.$$

A resistance of a part of the touch sensing electrode between a position where the touch sensing electrode is electrically connected to the corresponding fourth lead and a position where the touch sensing electrode is electrically connected to the third sub-lead is R5, a resistance of a part of the touch sensing electrode between a position where the touch sensing electrode is electrically connected to the corresponding fourth lead and a position where the touch sensing electrode is electrically connected to the fourth sub-lead is R6, a resistance of the third sub-lead is R7, a resistance of the fourth sub-lead is R8, and R5, R6, R7 and R8 satisfy $$2 \leq \frac{R5+R7}{R6+R8} \leq 9 \text{ or } 2 \leq \frac{R6+R8}{R5+R7} \leq 9.$$

In a possible implementation, in the touch structure according to the embodiments of the present disclosure, R1, R2, R3 and R4 satisfy $$\frac{R1+R3}{R2+R4} = 2 \text{ or } \frac{R2+R4}{R3+R5} = 2.$$

R5, R6, R7 and R8 satisfy $$\frac{R5+R7}{R6+R8} = 2 \text{ or } \frac{R6+R8}{R5+R7} = 2.$$

In a possible implementation, in the touch structure according to the embodiments of the present disclosure, each first lead has one terminal electrically connected to a corresponding touch driving electrode, and the other terminal electrically connected to a first wiring terminal in a binding area. Each second lead has one terminal electrically connected to a corresponding touch sensing electrode, and the other terminal electrically connected to a second wiring terminal in the binding area.

In a possible implementation, in the touch structure according to the embodiments of the present disclosure, each third lead is electrically connected to a terminal of a corresponding touch driving electrode which is not connected to the first lead. Each fourth lead is electrically connected to a terminal of a corresponding touch sensing electrode which is not connected to the second lead.

In a possible implementation, in the touch structure according to the embodiments of the present disclosure, the touch structure further comprises an insulating layer located over the touch driving electrodes and the touch sensing electrodes. The insulating layer has via holes penetrating therethrough at positions corresponding to test points for the touch driving electrodes and/or test points for the touch sensing electrodes.

The embodiments of the present disclosure further provide a touch panel. The touch panel comprises the touch structure according to various embodiments of the present disclosure described above.

The embodiments of the present disclosure further provide a display apparatus. The display apparatus comprises the touch panel according to various embodiments of the present disclosure described above.

The embodiments of the present disclosure further provide a test method for the touch structure according to various embodiments described above. The test method comprises: measuring, for each touch driving electrode, a resistance between a test point for the touch driving electrode and a first wiring terminal to determine whether there is an open circuit on the touch driving electrode and a corresponding first lead; and measuring, for each touch sensing electrode, a resistance between a test point for the touch sensing electrode and a second wiring terminal to determine whether there is an open circuit on the touch sensing electrode and a corresponding second lead.

In a possible implementation, in the test method according to the embodiments of the present disclosure, determining whether there is an open circuit on the touch driving electrode and a corresponding first lead comprises: when the measured resistance is R2+R4+R9, determining that there is an open circuit on a part of the touch driving electrode between a position where the touch driving electrode is electrically connected to the corresponding third lead and a position where the touch driving electrode is electrically connected to the first sub-lead and/or on the first sub-lead, wherein R9 is a resistance of the third lead; when the measured resistance is R1+R3+R9, determining that there is an open circuit on a part of the touch driving electrode between a position where the touch driving electrode is electrically connected to the corresponding third lead and a position where the touch driving electrode is electrically connected to the second sub-lead and/or on the second sub-lead, wherein R9 is the resistance of the third lead; when the measured resistance is abnormal, determining that there is an open circuit on the third lead corresponding to the touch driving electrode; and when the measured resistance is $$\frac{(R1+R3)\times(R2+R4)}{R1+R2+R3+R4}+R9,$$

determining that there is no open circuit on the touch driving electrode and the corresponding first lead, wherein R9 is the resistance of the third lead.

In a possible implementation, in the test method according to the embodiments of the present disclosure, determining whether there is an open circuit on the touch sensing electrode and a corresponding second lead comprises: when the measured resistance is R6+R8+R10, determining that there is an open circuit on a part of the touch sensing electrode between a position where the touch sensing electrode is electrically connected to the corresponding fourth lead and a position where the touch sensing electrode is electrically connected to the third sub-lead and/or on the third sub-lead, wherein R10 is a resistance of the fourth lead; when the measured resistance is R5+R7+R10, determining that there is an open circuit on a part of the touch sensing electrode between a position where the touch sensing electrode is electrically connected to the corresponding fourth lead and a position where the touch sensing electrode is electrically connected to the fourth sub-lead and/or on the fourth sub-lead, wherein R10 is the resistance of the fourth lead; when the measured resistance is abnormal, determining that there is an open circuit on the fourth lead corresponding to the touch sensing electrode; and when the measured resistance is $$\frac{(R5+R7)\times(R6+R8)}{R5+R6+R7+R8}+R10,$$

determining that there is no open circuit on the touch sensing electrode and the corresponding second lead, wherein R10 is the resistance of the fourth lead.

In a possible implementation, in the test method according to the embodiments of the present disclosure, determining whether there is an open circuit on the touch driving electrode and the corresponding first lead comprises: determining whether the measured resistance is abnormal; if the measured resistance is abnormal, determining that there is an open circuit on the touch driving electrode and/or the corresponding first lead and/or the corresponding third lead; and if the measured resistance is not abnormal, determining that there is no open circuit on the touch driving electrode and the corresponding first lead.

In a possible implementation, in the test method according to the embodiments of the present disclosure, determining whether there is an open circuit on the touch sensing electrode and the corresponding second lead comprises: determining whether the measured resistance is abnormal; if the measured resistance is abnormal, determining that there is an open circuit on the touch sensing electrode and/or the corresponding second lead and/or the corresponding fourth lead; and if the measured resistance is not abnormal, determining that there is no open circuit on the touch sensing electrode and the corresponding second lead.

The embodiments of the present disclosure provide a touch structure, a test method thereof, a touch panel and a display apparatus. In the touch structure, by taking touch driving electrodes as an example, a plurality of third leads which are insulated from each other and are in one-to-one correspondence with various touch driving electrodes are additionally provided, wherein each of the third leads has one terminal electrically connected to a corresponding touch driving electrode and the other terminal serving as a test point for testing whether there is an open circuit on the corresponding touch driving electrode and the corresponding first lead. In this way, two probes may be placed at a test point in a third lead and a first wiring terminal in a binding area respectively when an open circuit test is conducted on each of the touch driving electrodes and a corresponding first lead. As the probes need not to be electrically connected to the touch driving electrode, the open circuit test can be performed even if an insulating layer is laid over the touch driving electrode. This solution is particularly beneficial for a structure in which the touch driving electrode and a lead form a closed loop and a structure in which a lead is drawn from one terminal of the touch driving electrode.

BRIEF DESCRIPTION OF THE DRAWINGS

FIG. 5 is an equivalent circuit diagram of a second lead and a fourth lead corresponding to a touch sensing electrode in the touch structure illustrated in FIG. 2;

FIG. 6 is an equivalent circuit diagram of a first lead and a third lead corresponding to a touch driving electrode in the touch structure illustrated in FIG. 3;

FIG. 7 is a first flowchart of a test method for a touch structure according to an embodiment of the present disclosure;

DETAILED DESCRIPTION

The touch structure, the test method thereof, the touch panel and the display apparatus according to the embodiments of the present disclosure will be described in detail below with reference to the accompanying drawings.

Shapes and sizes of various components in the accompanying drawings do not represent true proportions thereof and are merely intended to schematically illustrate the present disclosure.

Figure 1:
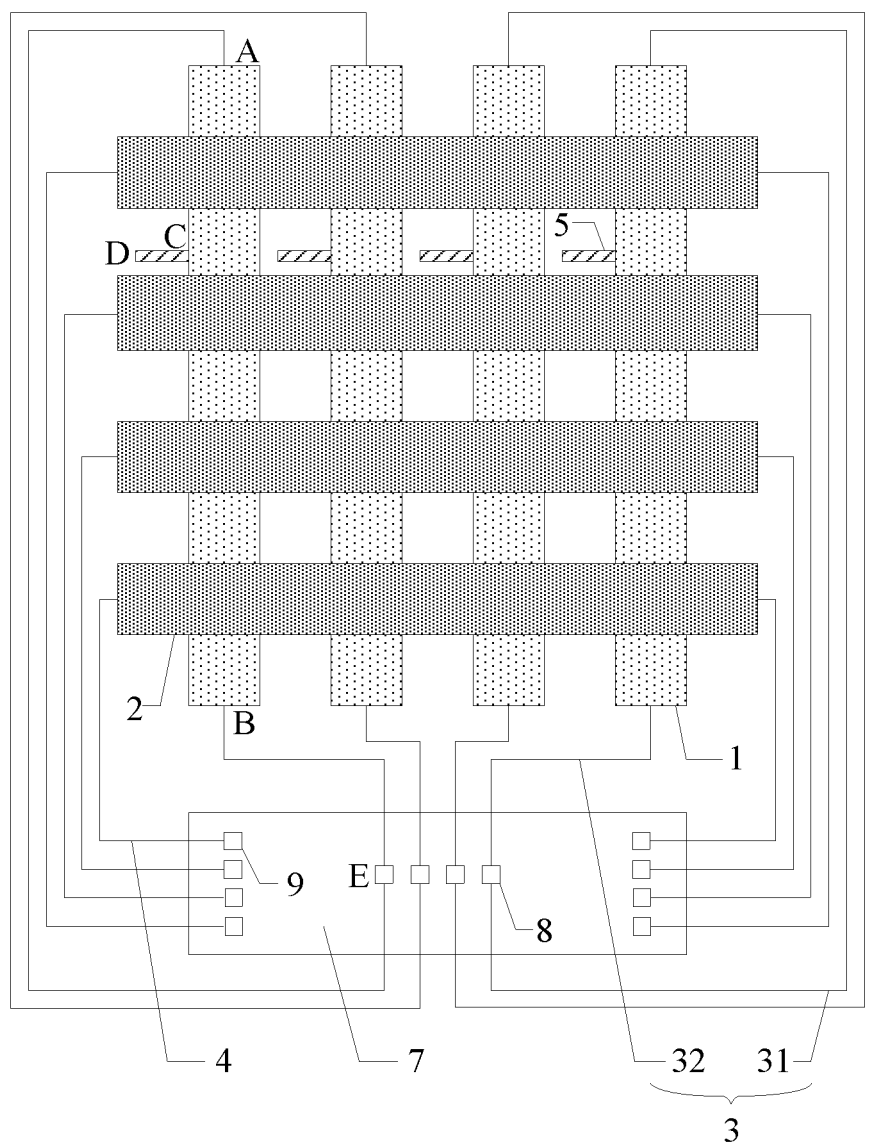
FIG. 1 is a first structural diagram of a touch structure according to an embodiment of the present disclosure.
Figure 2:
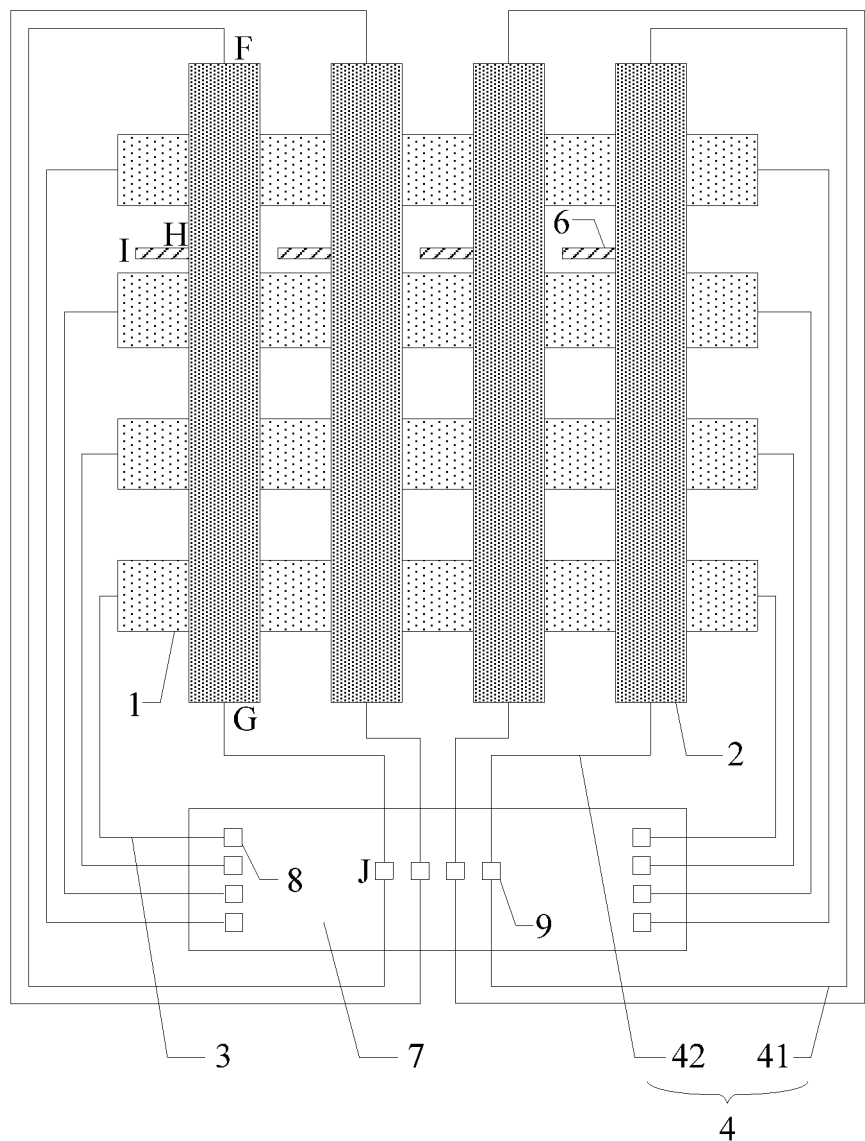
FIG. 2 is a second structural diagram of a touch structure according to an embodiment of the present disclosure.
Figure 3:
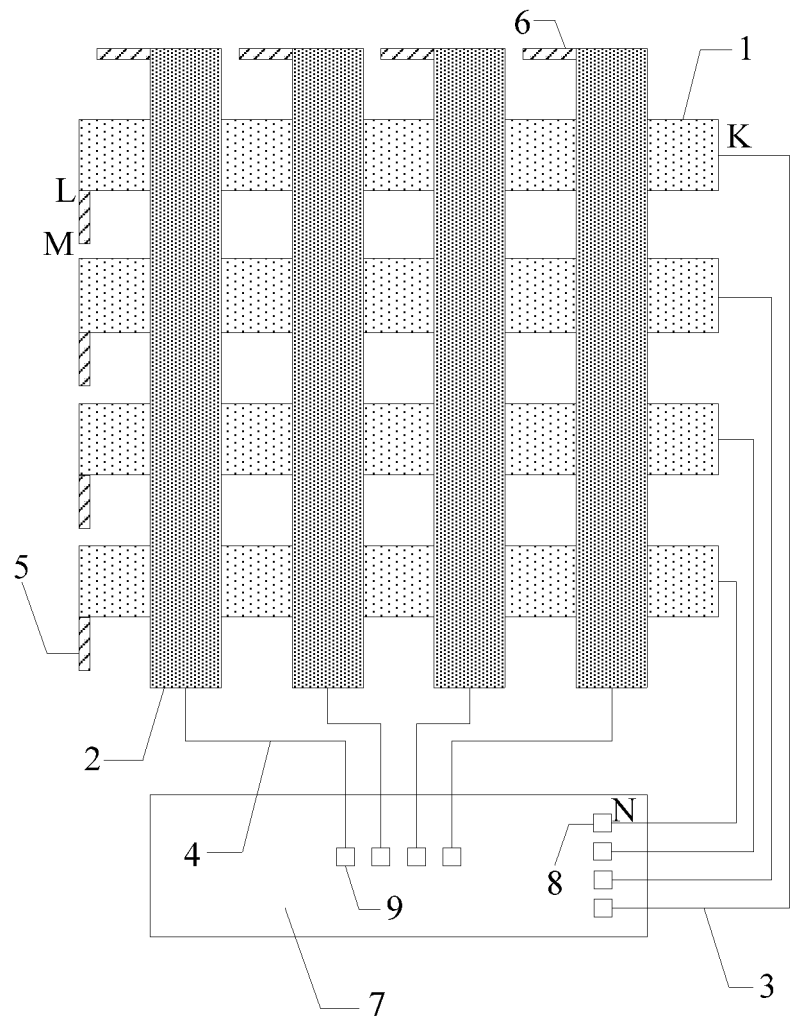
FIG. 3 is a third structural diagram of a touch structure according to an embodiment of the present disclosure.

The embodiments of the present disclosure provide a touch structure. As shown in FIGS. 1-3, the touch structure may comprise a plurality of touch driving electrodes 1 and a plurality of touch sensing electrodes 2 provided to intersect with the plurality of touch driving electrodes 1 in an insulating manner, a plurality of first leads 3 insulated from each other and electrically connected to various touch driving electrodes 1 in one-to-one correspondence, and a plurality of second leads 4 insulated from each other and electrically connected to various touch sensing electrodes 2 in one-to-one correspondence.

As shown in FIGS. 1 and 3, the touch structure may further comprise a plurality of third leads 5 insulated from each other and electrically connected to various touch driving electrodes 1 in one-to-one correspondence, wherein each of the third leads 5 has one terminal electrically connected to a corresponding touch driving electrode 1 and the other terminal serving as a test point for the touch driving electrode for testing whether there is an open circuit on the corresponding touch driving electrode 1 and the corresponding first lead 3.

As shown in FIGS. 2 and 3, the touch structure may further comprise a plurality of fourth leads 6 insulated from each other and corresponding to various touch sensing electrodes 2 in one-to-one correspondence, wherein each of the fourth leads 6 has one terminal electrically connected to a corresponding touch sensing electrode 2 and the other terminal serving as a test point for the touch sensing electrode for testing whether there is an open circuit on the corresponding touch sensing electrode 2 and the corresponding second lead 4.

In the touch structure according to the embodiments of the present disclosure, when an open circuit test is conducted on each of the touch driving electrodes 1 and a corresponding first lead 3 as shown in FIGS. 1 and 3, two probes may be placed at a test point in a third lead 5 corresponding to the touch driving electrode 1 and a first wiring terminal in a binding area electrically connected to the first lead 3 respectively. Similarly, when an open circuit test is conducted on each of the touch sensing electrodes 2 and a corresponding second lead 4 as shown in FIGS. 2 and 3, two probes may be placed at a test point in a fourth lead 6 corresponding to the touch sensing electrode 2 and a second wiring terminal in the binding area electrically connected to the second lead 4 respectively. As the probes need not to be electrically connected to the touch electrode, the open circuit test can be performed on the touch electrode and the leads thereof even if an insulating layer is laid over the touch electrode. This is particularly beneficial for a structure in which the touch electrode and a lead form a closed loop (as shown in FIG. 1, the touch driving electrode 1 and the corresponding first lead 3 form a closed loop, and as shown in FIG. 2, the touch sensing electrode 2 and the corresponding second lead 4 form a closed loop) and a structure in which a lead is drawn from one terminal of the touch electrode (as shown in FIG. 3, the first lead 3 is drawn from one terminal of the touch driving electrode 1 and the second lead 4 is drawn from one terminal of the touch sensing electrode 2).

It should be illustrated that, in the touch structure according to the embodiments of the present disclosure, as shown in FIG. 1, only the plurality of third leads 5 which are insulated from each other and are in one-to-one correspondence with various touch driving electrodes 1 may be provided. Alternatively, as shown in FIG. 2, only the plurality of fourth leads 6 which are insulated from each other and are in one-to-one correspondence with various touch sensing electrodes 2 may be provided. Alternatively, as shown in FIG. 3, the plurality of third leads 5 which are insulated from each other and are in one-to-one correspondence with various touch driving electrodes 1 and the plurality of fourth leads 6 which are insulated from each other and are in one-to-one correspondence with various touch sensing electrodes 2 may be provided. The present disclosure is not limited thereto.

Preferably, in the touch structure according to the embodiments of the present disclosure, in order to avoid the increase in a number of masking operations in the process of forming the touch structure and avoid the increase of fabrication processes of the touch structure, various third leads may be provided in a same layer as various touch driving electrodes, that is, various third leads and various touch driving electrodes are formed by the same patterning process using the same material. In this case, in order to avoid the problem that a short circuit occurs among various touch driving electrodes due to an electrical connection between each of the third leads and touch driving electrodes different from a corresponding touch driving electrode, a third lead corresponding to one of touch driving electrodes different from two outermost touch driving electrodes may be provided in a gap between the touch driving electrode and an adjacent touch driving electrode. For example, as shown in FIG. 1, in an order from left to right, a third lead 5 corresponding to a second touch driving electrode 1 is located in a gap between the second touch driving electrode 1 and a first touch driving electrode 1.

A third lead corresponding to one of the two outermost touch driving electrodes may be provided in a gap between the touch driving electrode and an adjacent touch driving electrode. Alternatively, a third lead corresponding to one of the two outermost touch driving electrodes may be provided on one side of the touch driving electrode away from the adjacent touch driving electrode. The present disclosure is not limited thereto. For example, as shown in FIG. 1, in an order from left to right, a third lead 5 corresponding to the first touch driving electrode 1 is located on one side of the first touch driving electrode 1 away from the second touch driving electrode 1, and a third lead 5 corresponding to a last touch driving electrode 1, i.e., a fourth touch driving electrode 1, is located in a gap between the fourth touch driving electrode 1 and a third touch driving electrode 1.

Similarly, in order to avoid the increase in a number of masks in the process of forming the touch structure and avoid the increase of fabrication processes of the touch structure, various fourth leads may be provided in a same layer as various touch sensing electrodes, that is, various fourth leads and various touch sensing electrodes are formed by the same patterning process using the same material. In this case, in order to avoid the problem that a short circuit occurs among various touch sensing electrodes due to an electrical connection between each of the fourth leads and touch sensing electrodes different from a corresponding touch sensing electrode, a fourth lead corresponding to one of touch sensing electrodes different from two outermost touch sensing electrodes may be provided in a gap between the touch sensing electrode and an adjacent touch sensing electrode. For example, as shown in FIG. 2, in an order from left to right, a fourth lead 6 corresponding to a second touch sensing electrode 2 is located in a gap between the second touch sensing electrode 2 and a first touch sensing electrode 2.

A fourth lead corresponding to one of the two outermost touch sensing electrodes may be provided in a gap between the touch sensing electrode and an adjacent touch sensing electrode. Alternatively, a fourth lead corresponding to one of the two outermost touch sensing electrodes may be provided on one side of the touch sensing electrode away from the adjacent touch sensing electrode. The present disclosure is not limited thereto. For example, as shown in FIG. 2, in an order from left to right, a fourth lead 6 corresponding to the first touch sensing electrode 2 is located on one side of the first touch sensing electrode 2 away from the second touch sensing electrode 2, and a fourth lead 6 corresponding to a last touch sensing electrode 2, i.e., a fourth touch sensing electrode 2, is located in a gap between the fourth touch sensing electrode 2 and a third touch sensing electrode 2.

In the touch structure according to the embodiments of the present disclosure, various third leads may also be provided in a different layer than various touch driving electrodes. That is, an insulating layer is provided between a layer where various third leads are located and a layer where various touch driving electrodes are located, and each of the third leads is electrically connected to a corresponding touch driving electrode through via holes penetrating through the insulating layer. Similarly, various fourth leads may also be provided in a different layer than various touch sensing electrodes. That is, an insulating layer is provided between a layer where various fourth leads are located and a layer where various touch sensing electrodes are located, and each of the fourth leads is electrically connected to a corresponding touch sensing electrode through via holes penetrating through the insulating layer. The present disclosure is also not limited thereto.

In a specific implementation, the touch structure according to the embodiments of the present disclosure may be applied to a structure in which the touch electrode and the corresponding lead are connected in any connection manner. Preferably, the touch structure according to the embodiments of the present disclosure may be any of the structures as shown in FIGS. 1 to 3. As shown in FIG. 1, each of the touch driving electrodes 1 and the corresponding first lead 3 form a closed loop. As shown in FIG. 2, each of the touch sensing electrodes 2 and the corresponding second lead 4 form a closed loop. As shown in FIG. 3, a first lead 3 is drawn from one terminal of each of the touch driving electrodes 1 and a second lead 4 is drawn from one terminal of each of the touch sensing electrodes 2. The touch structure according to the embodiments of the present disclosure is not limited to any of the structures shown in FIGS. 1 to 3, and there may also be other types of connection manners for the touch electrode and the lead. For example, leads are drawn from two terminals of the touch electrode respectively, and the two leads are electrically connected to two wiring terminals in a binding area respectively. The present disclosure is not limited thereto. Specific implementations when the touch structure according to the embodiments of the present disclosure is applied to the three structures respectively will be described in detail below through three specific examples.

First example: each of the touch driving electrodes and a corresponding first lead form a closed loop.

In a specific implementation, in the touch structure according to the embodiments of the present disclosure, as shown in FIG. 1, each of the first leads 3 may comprise a first sub-lead 31 and a second sub-lead 32. Each of the touch driving electrodes 1 has one terminal electrically connected to one terminal of a first sub-lead 31 of a corresponding first lead 3, and the other terminal electrically connected to one terminal of a second sub-lead 32 of the corresponding first lead 3, the other terminal of the first sub-lead 31 is electrically connected to the other terminal of the second sub-lead 32, and both the other terminal of the first sub-lead 31 and the other terminal of the second sub-lead 32 are electrically connected to a first wiring terminal 8 in a binding area 7. In this way, each of the touch driving electrodes 1 and the corresponding first lead 3 form a closed loop.

It should be illustrated that, in the touch structure as shown in FIG. 1, as both the first sub-lead 31 and the second sub-lead 32 of the first lead 3 are electrically connected to the first wiring terminal 8 located in the binding area 7 and various first leads 3 are generally provided in a same layer as various second leads 4, in order to avoid the problem that a short circuit occurs between various first leads 3 and various second leads 4, as shown in FIG. 1, a connection between each of the touch sensing electrodes 2 and a corresponding second lead 4 may a structure in which leads are drawn from two terminals of each of the touch sensing electrodes 2 respectively, and the two drawn leads are electrically connected to two second wiring terminals 9 in the binding area 7 respectively. The connection between each of the touch sensing electrodes and the corresponding second lead may also be a structure in which a lead is drawn from one terminal of each of the touch sensing electrodes, and the drawn lead is electrically connected to a second wiring terminal in the binding area. Alternatively, the connection between each of the touch sensing electrodes and the corresponding second lead may also be a structure in which a closed loop is formed. The present disclosure is not limited thereto, as long as various first leads are insulated from various second leads.

Preferably, the touch structure according to the embodiments of the present disclosure is particularly applicable to a condition in which an insulating layer is provided on various touch driving electrodes and various touch sensing electrodes, and the insulating layer has via holes penetrating therethrough at positions corresponding to various test points (including test points for the touch driving electrodes and/or test points for the touch sensing electrodes), i.e., there are via holes in the insulating layer through which various test points are exposed. This is because the insulating layer covers various touch driving electrodes, which may result in that when an open circuit test is conducted on each of the touch driving electrodes and the corresponding first lead, two probes cannot be placed at a first wiring terminal in a binding area and the touch driving electrode respectively. Based thereon, in the touch structure according to the embodiments of the present disclosure, a plurality of third leads which are insulated from each other and are in one-to-one correspondence with various touch driving electrodes are additionally provided, wherein each of the third leads has one terminal electrically connected to a corresponding touch driving electrode and the other terminal serving as a test point for testing whether there is an open circuit on the corresponding touch driving electrode and the corresponding first lead. In this way, when an open circuit test is conducted on each of the touch driving electrodes and the corresponding first lead in the touch structure according to the embodiments of the present disclosure, two probes may be placed at a first wiring terminal in a binding area which is electrically connected to the first lead and a test point in the third lead corresponding to the touch driving electrode respectively, and it may be determined whether there is an open circuit on each of the touch driving electrodes and the corresponding first lead by testing a resistance between the two probes.

Figure 4:
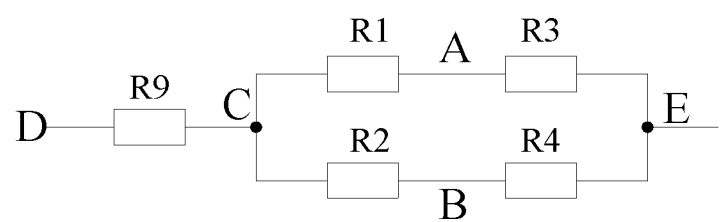
FIG. 4 is an equivalent circuit diagram of a first lead and a third lead corresponding to a touch driving electrode in the touch structure illustrated in FIG. 1.

The principle of performing the open circuit test on each of the touch driving electrodes and the corresponding first lead in the touch structure according to the embodiments of the present disclosure will be described in detail below. As shown in FIG. 1, a position where the touch driving electrode 1 is electrically connected to the first sub-lead 31 of the corresponding first lead 3 is denoted as A, and a position where the touch driving electrode 1 is electrically connected to the second sub-lead 32 of the corresponding first lead 3 is denoted as B, a position where the touch driving electrode 1 is electrically connected to the corresponding third lead 5 is denoted as C, a test point in the third lead 5 is denoted as D, and a position of the first wiring terminal 8 electrically connected to the first sub-lead 31 and the second sub-lead 32 of the first lead 3 is denoted as E. It is assumed that a resistance of each of the touch driving electrodes 1 between a position where the touch driving electrode 1 is electrically connected to the corresponding third lead 5 and a position where the touch driving electrode 1 is electrically connected to the first sub-lead 31, i.e., a resistance of the touch driving electrode 1 between C and A is R1, a resistance of each of the touch driving electrodes 1 between a position where the touch driving electrode 1 is electrically connected to the corresponding third lead 5 and a position where the touch driving electrode 1 is electrically connected to the second sub-lead 32, i.e., a resistance of the touch driving electrode 1 between C and B is R2, a resistance of each of the first sub-leads 31, i.e., a resistance of the first lead 3 between A and E is R3, a resistance of each of the second sub-leads 32, i.e., a resistance of the first lead 3 between B and E is R4, and a resistance of each of the third leads 5, i.e., a resistance between C and D is R9. In this case, when two probes are placed at the test point D and the first wiring terminal E respectively, an equivalent circuit diagram between the two probes is as shown in FIG. 4. When an open circuit test is conducted on the touch driving electrode 1 and the corresponding first lead 3, the following four conditions may occur: when there is an open circuit between C and D, the measured resistance R between the two probes is very large, which causes an abnormal result; when there is an open circuit between B and C or there is an open circuit between B and E, the measured resistance between the two probes is R=R1+R3+R9; when there is an open circuit between A and C or there is an open circuit between A and E, the measured resistance between the two probes is R=R2+R4+R9; and when there is no open circuit, the measured resistance between the two probes is $$R = \frac{(R1+R3) \times (R2+R4)}{R1+R2+R3+R4} + R9.$$

Therefore, it may be determined whether there is an open circuit in the closed loop formed by the touch driving electrode and the corresponding first lead and a position of a point where the open circuit occurs by measuring the resistance R between the two probes.

It should be illustrated that, in the touch structure according to the embodiments of the present disclosure, as shown in FIG. 1, an open circuit test can be performed on each of the touch sensing electrodes 2 and the corresponding second lead 4 as long as two probes are provided at two second wiring terminals 9 electrically connected to the second lead 4 respectively. In this case, it may be determined whether there is an open circuit on the touch sensing electrode 2 and the corresponding second lead 4 by measuring a resistance between the two probes. When the measured resistance between the two probes is very large which causes an abnormal result, it is determined that there is a point where an open circuit occurs between the touch sensing electrode 2 and the corresponding second lead 4; and when the measured resistance between the two probes is a sum of a resistance of the touch sensing electrode 2 and a resistance of the corresponding second lead 4, it is determined that there is no point where an open circuit occurs between the touch sensing electrode 2 and the corresponding second lead 4.

Preferably, in the touch structure according to the embodiments of the present disclosure, in order to facilitate determining the position of the point where the open circuit occurs in the closed loop formed by the touch driving electrode and the corresponding first lead according to value of the measured resistance between the two probes, the position C where the touch driving electrode is electrically connected to the corresponding third lead may be designed. Specifically, value of R1 and R1 may be adjusted by adjusting the position C, and value of R3 and R4 is determined after the position D of the first wiring terminal is determined. Therefore, value of $$\frac{R1+R3}{R2+R4}$$

may be adjusted by adjusting the position C. When R1, R2, R3, and R4 satisfy $$2 \le \frac{R1+R3}{R2+R4} \le 9 \text{ or } 2 \le \frac{R2+R4}{R1+R3} \le 9,$$

it is easy to determine the position of the point where the open circuit occurs in the closed loop formed by the touch driving electrode and the corresponding first lead according to the value of the measured resistance R between the two probes.

Preferably, in the touch structure according to the embodiments of the present disclosure, R1, R2, R3, and R4 may satisfy $$\frac{R1+R3}{R2+R4} = 2 \text{ or } \frac{R2+R4}{R1+R3} = 2.$$

Second example: each of the touch sensing electrodes and a corresponding second lead form a closed loop.

In a specific implementation, in the touch structure according to the embodiments of the present disclosure, as shown in FIG. 2, each of the second leads 4 may comprise a third sub-lead 41 and a fourth sub-lead 42. Each of the touch sensing electrodes 2 has one terminal electrically connected to one terminal of a third sub-lead 41 of a corresponding second lead 4, and the other terminal electrically connected to one terminal of a fourth sub-lead 42 of the corresponding second lead 4, the other terminal of the third sub-lead 41 is electrically connected to the other terminal of the fourth sub-lead 42, and both the other terminal of the third sub-lead 41 and the other terminal of the fourth sub-lead 42 are electrically connected to a second wiring terminal 9 in a binding area 7. In this way, each of the touch sensing electrodes 2 and the corresponding second lead 4 form a closed loop.

It should be illustrated that, in the touch structure as shown in FIG. 2, as both the third sub-lead 41 and the fourth sub-lead 42 of the second lead 4 are electrically connected to the second wiring terminal 9 located in the binding area 7 and various first leads 3 are generally provided in a same layer as various second leads 4, in order to avoid the problem that a short circuit occurs between various first leads 3 and various second leads 4, as shown in FIG. 2, a connection between each of the touch driving electrodes 1 and a corresponding first lead 3 may a structure in which leads are drawn from two terminals of each of the touch driving electrodes 1 respectively, and the two drawn leads are electrically connected to two first wiring terminals 8 in the binding area 7 respectively. The connection between each of the touch driving electrodes and the corresponding first lead may also be a structure in which a lead is drawn from one terminal of each of the touch driving electrodes, and the drawn lead is electrically connected to a first wiring terminal in the binding area. Alternatively, the connection between each of the touch driving electrodes and the corresponding first lead may also be a structure in which a closed loop is formed. The present disclosure is not limited thereto, as long as various first leads are insulated from various second leads.

Preferably, the touch structure according to the embodiments of the present disclosure is particularly applicable to a condition in which an insulating layer is provided on various touch driving electrodes and various touch sensing electrodes, and the insulating layer has via holes penetrating therethrough at positions corresponding to various test points (including test points for the touch driving electrodes and/or test points for the touch sensing electrodes), i.e., there are via holes in the insulating layer through which various test points are exposed. This is because the insulating layer covers various touch sensing electrodes, which may result in that when an open circuit test is conducted on each of the touch sensing electrodes and the corresponding second lead, two probes cannot be placed at a second wiring terminal in a binding area and the touch sensing electrode respectively. Based thereon, in the touch structure according to the embodiments of the present disclosure, a plurality of fourth leads which are insulated from each other and are in one-to-one correspondence with various touch sensing electrodes are additionally provided, wherein each of the fourth leads has one terminal electrically connected to a corresponding touch sensing electrode and the other terminal serving as a test point for testing whether there is an open circuit on the corresponding touch sensing electrode and the corresponding second lead. When an open circuit test is conducted on each of the touch sensing electrodes and the corresponding second lead in the touch structure according to the embodiments of the present disclosure, two probes may be placed at a second wiring terminal in a binding area which is electrically connected to the second lead and a test point in the fourth lead corresponding to the touch sensing electrode respectively, and it may be determined whether there is an open circuit on each of the touch sensing electrodes and the corresponding second lead by testing a resistance between the two probes.

The principle of performing the open circuit test on each of the touch sensing electrodes and the corresponding second lead in the touch structure according to the embodiments of the present disclosure will be described in detail below. As shown in FIG. 2, a position where the touch sensing electrode 2 is electrically connected to the third sub-lead 41 of the corresponding second lead 4 is denoted as F, and a position where the touch sensing electrode 2 is electrically connected to the fourth sub-lead 42 of the corresponding second lead 4 is denoted as G, a position where the touch sensing electrode 2 is electrically connected to the corresponding fourth lead 6 is denoted as H, a test point in the fourth lead 6 is denoted as I, and a position of the second wiring terminal 9 electrically connected to the third sub-lead 41 and the fourth sub-lead 42 of the second lead 4 is denoted as J. It is assumed that a resistance of each of the touch sensing electrodes 2 between a position where the touch sensing electrode 2 is electrically connected to the corresponding fourth lead 6 and a position where the touch sensing electrode 2 is electrically connected to the third sub-lead 41, i.e., a resistance of the touch sensing electrode 2 between H and F is R5, a resistance of each of the touch sensing electrodes 2 between a position where the touch sensing electrode 2 is electrically connected to the corresponding fourth lead 6 and a position where the touch sensing electrode 2 is electrically connected to the fourth sub-lead 42, i.e., a resistance of the touch sensing electrode 2 between H and G is R6, a resistance of each of the third sub-leads 41, i.e., a resistance of the second lead 4 between F and J is R7, a resistance of each of the fourth sub-leads 42, i.e., a resistance of the second lead 4 between G and J is R8, and a resistance of each of the fourth leads 6, i.e., a resistance between H and I is R10. In this case, when two probes are placed at the test point I and the second wiring terminal J respectively, an equivalent circuit diagram between the two probes is as shown in FIG. 5. When an open circuit test is conducted on the touch sensing electrode 2 and the corresponding second lead 4, the following four conditions may occur: when there is an open circuit between H and I, the measured resistance R between the two probes is very large, which causes an abnormal result; when there is an open circuit between G and H or there is an open circuit between G and J, the measured resistance between the two probes is R=R5+R7+R10; when there is an open circuit between F and H or there is an open circuit between F and J, the measured resistance between the two probes is R=R6+R8+R10; and when there is no open circuit, the measured resistance between the two probes is R=

$$\frac{(R5+R7)\times(R6+R8)}{R5+R6+R7+R8}+R10.$$

Therefore, it may be determined whether there is an open circuit in the closed loop formed by the touch sensing electrode and the corresponding second lead and a position of a point where the open circuit occurs by measuring the resistance R between the two probes.

It should be illustrated that, in the touch structure according to the embodiments of the present disclosure, as shown in FIG. 2, an open circuit test can be performed on each of the touch driving electrodes 1 and the corresponding first lead 3 as long as two probes are provided at two first wiring terminals 8 electrically connected to the first lead 3 respectively. In this case, it may be determined whether there is an open circuit on the touch driving electrode 1 and the corresponding first lead 3 by measuring a resistance between the two probes. When the measured resistance between the two probes is very large which causes an abnormal result, it is determined that there is a point where an open circuit occurs between the touch driving electrode 1 and the corresponding first lead 3; and when the measured resistance between the two probes is a sum of a resistance of the touch driving electrode 1 and a resistance of the corresponding first lead 3, it is determined that there is no point where an open circuit occurs between the touch driving electrode 1 and the corresponding first lead 3.

Preferably, in the touch structure according to the embodiments of the present disclosure, in order to facilitate determining the position of the point where the open circuit occurs in the closed loop formed by the touch sensing electrode and the corresponding second lead according to value of the measured resistance between the two probes, the position H where the touch sensing electrode is electrically connected to the corresponding fourth lead may be designed. Specifically, value of R5 and R6 may be adjusted by adjusting the position H, and value of R7 and R8 is determined after the position I of the first wiring terminal is determined. Therefore, value of $$\frac{R5+R7}{R6+R8}$$

may be adjusted by adjusting the position H. When R5, R6, R7, and R8 satisfy $$2 \leq \frac{R5 + R7}{R6 + R8} \leq 9 \text{ or } 2 \leq \frac{R6 + R8}{R5 + R7} \leq 9,$$

it is easy to determine the position of the point where the open circuit occurs in the closed loop formed by the touch sensing electrode and the corresponding second lead according to the value of the measured resistance R between the two probes.

Preferably, in the touch structure according to the embodiments of the present disclosure, R5, R6, R7, and R8 may satisfy $$\frac{R5 + R7}{R6 + R8} = 2 \text{ or } \frac{R6 + R8}{R5 + R7} = 2.$$

Third example: one first lead is drawn from one terminal of each of the touch driving electrodes, and one second lead is drawn from one terminal of each of the touch sensing electrodes.

In a specific implementation, in the touch structure according to the embodiments of the present disclosure, as shown in FIG. 3, each of the first leads 3 has one terminal electrically connected to a corresponding touch driving electrode 1, and the other terminal electrically connected to a first wiring terminal 8 in a binding area 7, that is, a connection between each of the touch driving electrodes 1 and a corresponding first lead 3 is a structure in which one first lead 3 is drawn from each of the touch driving electrodes 1; and each of the second leads 4 has one terminal electrically connected to a corresponding touch sensing electrode 2, and the other terminal electrically connected to a second wiring terminal 9 in the binding area 7, that is, a connection between each of the touch sensing electrodes 2 and a corresponding second lead 4 is a structure in which one second lead 4 is drawn from each of the touch sensing electrodes 2.

In a specific implementation, in the touch structure according to the embodiments of the present disclosure, as shown in FIG. 3, each of the third leads 5 may be electrically connected to one terminal of the corresponding touch driving electrode 1 which is not connected to the first lead 3, that is, each of the touch driving electrodes 1 has one terminal electrically connected to the corresponding first lead 3, and the other terminal electrically connected to the corresponding third lead 5. Thus, when an open circuit test is conducted on each of the touch driving electrodes 1 and the corresponding first lead 3, two probes may be placed at a first wiring terminal 8 in a binding area 7 and a test point in a third lead 5 respectively, and an open circuit test may be performed on the entire touch driving electrode 1 and the corresponding first lead 3 by measuring a resistance between the two probes. Each of the fourth leads 6 is electrically connected to one terminal of the corresponding touch sensing electrode 2 which is not connected to the second lead 4, that is, each of the touch sensing electrodes 2 has one terminal electrically connected to the corresponding second lead 4, and the other terminal electrically connected to the corresponding fourth lead 6. Thus, when an open circuit test is conducted on each of the touch sensing electrodes 2 and the corresponding second lead 4, two probes may be placed at a second wiring terminal 9 in the binding area 7 and a test point in a fourth lead 6 respectively, and an open circuit test may be performed on the entire touch sensing electrode 2 and the corresponding second lead 4 by measuring a resistance between the two probes.

The principle of performing the open circuit test on each of the touch driving electrodes and the corresponding first lead in the touch structure according to the embodiments of the present disclosure will be described in detail below. As shown in FIG. 3, a position where the touch driving electrode 1 is electrically connected to the corresponding first lead 3 is denoted as K, a position where the touch driving electrode 1 is electrically connected to the corresponding third lead 5 is denoted as L, a position of a test point in the third lead 5 is denoted as M, and a position of a first wiring terminal 8 electrically connected to the first lead 3 is denoted as N. It is assumed that a resistance of each of the touch driving electrodes 1, i.e., a resistance between K and L is R11, a resistance of each of the first leads 3, i.e., a resistance between K and N is R12, and a resistance of each of the third leads 5, i.e., a resistance between M and L is R9. Thus, when two probes are placed at the test point M and the first wiring terminal N respectively, an equivalent circuit diagram between the two probes is shown in FIG. 6. When an open circuit test is conducted on the touch driving electrode 1 and the corresponding first lead 3, the following two cases may occur: when there is an open circuit between M and L or there is an open circuit between L and K (that is, there is a point where an open circuit occurs in the touch driving electrode) or there is an open circuit between K and N (that is, there is a point where an open circuit occurs in the first lead), the measured resistance R between the two probes is very large, which causes an abnormal result; and when there is no open circuit, the measured resistance between the two probes is R=R9+R11+R12. Therefore, it may be determined whether there is an open circuit on the touch driving electrode and the corresponding first lead and a position of a point where an open circuit occurs by measuring the resistance R between the two probes.

It should be illustrated that the principle of performing the open circuit test on each of the touch sensing electrodes and the corresponding second lead in the touch structure according to the embodiments of the present disclosure is similar to the principle of performing the open circuit test on each of the touch driving electrodes and the corresponding first lead, and the repeated descriptions will not be described again.

Preferably, the touch structure according to the embodiments of the present disclosure is particularly applicable to a condition in which an insulating layer is provided on various touch driving electrodes and various touch sensing electrodes, and the insulating layer has via holes penetrating therethrough at positions corresponding to various test points (including test points for the touch driving electrodes and/or test points for the touch sensing electrodes), i.e., there are via holes in the insulating layer through which various test points are exposed. This is because the insulating layer covers various touch driving electrodes and various touch sensing electrodes, which may result in that when an open circuit test is conducted on each of the touch driving electrodes and the corresponding first lead, two probes cannot be placed at a first wiring terminal in a binding area and the touch driving electrode respectively, and when an open circuit test is conducted on each of the touch sensing electrodes and the corresponding second lead, two probes cannot be placed at a second wiring terminal in the binding area and the touch sensing electrode respectively. Based thereon, in the touch structure according to the embodiments of the present disclosure, a plurality of third leads which are insulated from each other and are in one-to-one correspondence with various touch driving electrodes and a plurality of fourth leads which are insulated from each other and are in one-to-one correspondence with various touch sensing electrodes are additionally provided, wherein each of the third leads has one terminal electrically connected to a corresponding touch driving electrode and the other terminal serving as a test point for testing whether there is an open circuit on the corresponding touch driving electrode and the corresponding first lead, and each of the fourth leads has one terminal electrically connected to a corresponding touch sensing electrode and the other terminal serving as a test point for testing whether there is an open circuit on the corresponding touch sensing electrode and the corresponding second lead. In this way, when an open circuit test is conducted on each of the touch driving electrodes and the corresponding first lead in the touch structure according to the embodiments of the present disclosure, two probes may be placed at a first wiring terminal in a binding area which is electrically connected to the first lead and a test point in the third lead corresponding to the touch driving electrode respectively, and it may be determined whether there is an open circuit on each of the touch driving electrodes and the corresponding first lead by testing a resistance between the two probes. When an open circuit test is conducted on each of the touch sensing electrodes and the corresponding second lead in the touch structure according to the embodiments of the present disclosure, two probes may be placed at a second wiring terminal in a binding area which is electrically connected to the second lead and a test point in the fourth lead corresponding to the touch sensing electrode respectively, and it may be determined whether there is an open circuit on each of the touch sensing electrodes and the corresponding second lead by testing a resistance between the two probes.

With respect to the touch structure according to the embodiments of the present disclosure, the embodiments of the present disclosure further provide a test method for a touch structure, as shown in FIG. 7, comprising the following steps.

In S701, measuring, for each touch driving electrode, a resistance between a test point for the touch driving electrode and a first wiring terminal to determine whether there is an open circuit on the touch driving electrode and a corresponding first lead.

In S702, measuring, for each touch sensing electrode, a resistance between a test point for the touch sensing electrode and a second wiring terminal to determine whether there is an open circuit on the touch sensing electrode and a corresponding second lead.

It should be illustrated that the test method according to the embodiments of the present disclosure may be applicable to performing an open circuit test on each of touch driving electrodes and a lead thereof, and each of touch sensing electrodes and a lead thereof in any touch structure. Preferably, it is particularly suitable for performing an open circuit test on a structure in which a closed loop is formed by each of the touch driving electrodes and a lead thereof, and/or a closed loop is formed by each of the touch sensing electrodes and a lead thereof, and an insulating layer is laid over various touch driving electrodes and various touch sensing electrodes; or is particularly suitable for performing an open circuit test on a structure in which a lead is drawn from one terminal of each of the touch driving electrodes and/or a lead is drawn from one terminal of each of the touch sensing electrodes and an insulating layer is laid over various touch driving electrodes and various touch sensing electrodes.

In a specific implementation, in the test method according to the embodiments of the present disclosure, step S701 and step S702 are not performed in any particular order. Step S701 may be firstly performed and then step S702 may be performed. Alternatively, step S702 may also be firstly performed and then step S701 may be performed. The present disclosure is not limited thereto.

In a specific implementation, step S701 in the test method according the embodiments of the present disclosure may specifically be implemented by:

when the measured resistance is R2+R4+R9, determining that there is an open circuit on a part of the touch driving electrode between a position where the touch driving electrode is electrically connected to the corresponding third lead and a position where the touch driving electrode is electrically connected to the first sub-lead and/or on the first sub-lead, wherein R9 is a resistance of the third lead;

when the measured resistance is R1+R3+R9, determining that there is an open circuit on a part of the touch driving electrode between a position where the touch driving electrode is electrically connected to the corresponding third lead and a position where the touch driving electrode is electrically connected to the second sub-lead and/or on the second sub-lead, wherein R9 is the resistance of the third lead;

when the measured resistance is abnormal, determining that there is an open circuit on the third lead corresponding to the touch driving electrode; and when the measured resistance is $$\frac{(R1+R3)\times(R2+R4)}{R1+R2+R3+R4}+R9,$$

determining that there is no open circuit on the touch driving electrode and the corresponding first lead, wherein R9 is the resistance of the third lead.

In a specific implementation, step S702 in the test method according the embodiments of the present disclosure may specifically be implemented by:

when the measured resistance is R6+R8+R10, determining that there is an open circuit on a part of the touch sensing electrode between a position where the touch sensing electrode is electrically connected to the corresponding fourth lead and a position where the touch sensing electrode is electrically connected to the third sub-lead and/or on the third sub-lead, wherein R10 is a resistance of the fourth lead;

when the measured resistance is R5+R7+R10, determining that there is an open circuit on a part of the touch sensing electrode between a position where the touch sensing electrode is electrically connected to the corresponding fourth lead and a position where the touch sensing electrode is electrically connected to the fourth sub-lead and/or on the fourth sub-lead, wherein R10 is the resistance of the fourth lead;

when the measured resistance is abnormal, determining that there is an open circuit on the fourth lead corresponding to the touch sensing electrode; and when the measured resistance is $$\frac{(R5+R7)\times(R6+R8)}{R5+R6+R7+R8}+R10,$$

determining that there is no open circuit on the touch sensing electrode and the corresponding second lead, wherein R10 is the resistance of the fourth lead.

Figure 8:
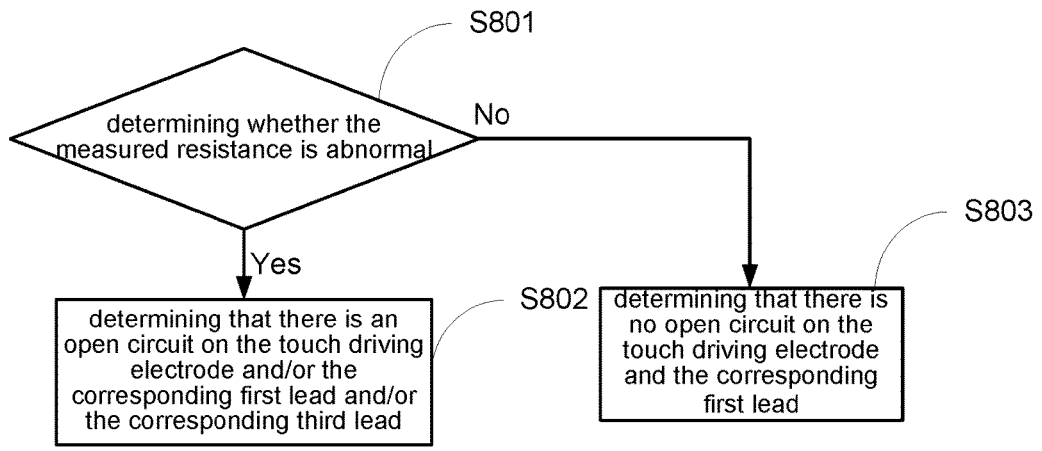
FIG. 8 is a second flowchart of a test method for a touch structure according to an embodiment of the present disclosure.

In a specific implementation, as shown in FIG. 8, step S701 in the test method according to the embodiments of the present disclosure may specifically comprise the following steps.

In S801, determining whether the measured resistance is abnormal; and if so, step S802 is performed, and if not, step S803 is performed.

In S802, determining that there is an open circuit on the touch driving electrode and/or the corresponding first lead and/or the corresponding third lead.

In S803, determining that there is no open circuit on the touch driving electrode and the corresponding first lead.

Figure 9:
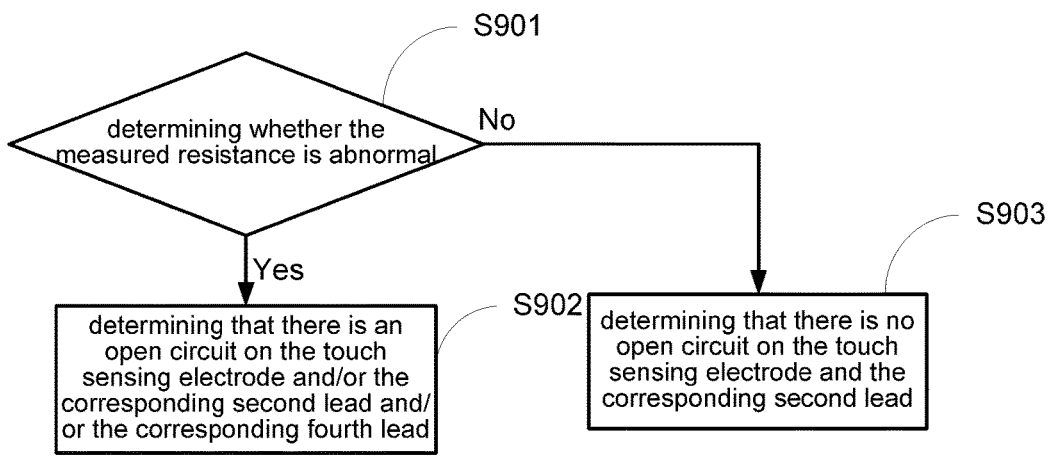
FIG. 9 is a third flowchart of a test method for a touch structure according to an embodiment of the present disclosure.

In a specific implementation, as shown in FIG. 9, step S702 in the test method according to the embodiments of the present disclosure may specifically comprise the following steps.

In S901, determining whether the measured resistance is abnormal; and if so, step S902 is performed, and if not, step S903 is performed.

In S902, determining that there is an open circuit on the touch sensing electrode and/or the corresponding second lead and/or the corresponding fourth lead.

In S903, determining that there is no open circuit on the touch sensing electrode and the corresponding second lead.

It should be illustrated that, specific implementation of the test method according to the embodiments of the present disclosure can be known with reference to the embodiments of the touch structure according to the embodiments of the present disclosure, and repeated descriptions thereof are not described again.

Based on the same concept, the embodiments of the present disclosure further provide a touch panel comprising the touch structure according to the embodiments of the present disclosure. Implementations of the touch panel can be known with reference to the embodiments of the touch structure, and repeated descriptions thereof are not described again.

In a specific implementation, the touch panel according to the embodiments of the present disclosure may be an add on mode touch panel; and alternatively, the touch panel may also be an on cell touch panel or an in cell touch panel. The present disclosure is not limited thereto.

Based on the same concept, the embodiments of the present disclosure further provide a display apparatus comprising the touch panel according to the embodiments of the present disclosure. The display apparatus may be any product or component having a display function, such as a mobile phone, a tablet computer, a television, a display, a notebook computer, a digital photo frame, a navigator etc. Implementations of the display apparatus can be known with reference to the embodiments of the touch panel, and repeated descriptions thereof are not described again.

The embodiments of the present disclosure provide a touch structure, a test method thereof, a touch panel and a display apparatus. In the touch structure, by taking touch driving electrodes as an example, a plurality of third leads which are insulated from each other and are in one-to-one correspondence with various touch driving electrodes are additionally provided, wherein each of the third leads has one terminal electrically connected to a corresponding touch driving electrode and the other terminal serving as a test point for testing whether there is an open circuit on the corresponding touch driving electrode and the corresponding first lead. In this way, two probes may be placed at a test point in a third lead and a first wiring terminal in a binding area respectively when an open circuit test is conducted on each of the touch driving electrodes and a corresponding first lead. As the probes need not to be electrically connected to the touch driving electrode, the open circuit test can be performed even if an insulating layer is laid over the touch driving electrode. This is particularly beneficial for a structure in which the touch driving electrode and a lead form a closed loop and a structure in which a lead is drawn from one terminal of the touch driving electrode.

Obviously, those skilled in the art can make various modifications and variations to the present disclosure without departing from the spirit and scope of the present disclosure. In this way, if these modifications and variations of the present disclosure fall within the scope of the claims of the present disclosure and equivalent technologies thereof, these modifications and variations are also intended to be included in the present disclosure.

We claim:

1. A touch structure, comprising:
a plurality of touch driving electrodes;
a plurality of touch sensing electrodes provided to intersect with the plurality of touch driving electrodes in an insulating manner;
a plurality of first leads insulated from each other and electrically connected to the touch driving electrodes in one-to-one correspondence;
a plurality of second leads insulated from each other and electrically connected to the touch sensing electrodes in one-to-one correspondence;
a plurality of third leads insulated from each other and in one-to-one correspondence with the touch driving electrodes, wherein each third lead has one terminal electrically connected to a corresponding touch driving electrode and the other terminal serving as a test point for the touch driving electrode for testing whether there is an open circuit on the corresponding touch driving electrode and a corresponding first lead; and/or
a plurality of fourth leads insulated from each other and in one-to-one correspondence with the touch sensing electrodes, wherein each fourth lead has one terminal electrically connected to a corresponding touch sensing electrode and the other terminal serving as a test point for the touch sensing electrode for testing whether there is an open circuit on the corresponding touch sensing electrode and a corresponding second lead,
wherein:
each of the first leads comprises a first sub-lead and a second sub-lead, wherein each of the touch driving electrodes has a first terminal electrically connected to a first terminal of a first sub-lead of a corresponding first lead, and a second terminal electrically connected to a first terminal of a second sub-lead of the corresponding first lead, a second terminal of the first sub-lead is electrically connected to a second terminal of the second sub-lead, and both the second terminal of the first sub-lead and the second terminal of the second sub-lead are electrically connected to a first wiring terminal in a binding area, and
a resistance of a part of the touch driving electrode between a position where the touch driving electrode is electrically connected to the corresponding third lead and a position where the touch driving electrode is electrically connected to the first sub-lead is R1, a resistance of a part of the touch driving electrode between a position where the touch driving electrode is electrically connected to the corresponding third lead and a position where the touch driving electrode is electrically connected to the second sub-lead is R2, a resistance of the first sub-lead is R3, a resistance of the second sub-lead is R4, and R1, R2, R3 and R4 satisfy $$2 \le \frac{R1+R3}{R2+R4} \le 9 \text{ or } 2 \le \frac{R2+R4}{R1+R3} \le 9;$$

and or
each of the second leads comprises a third sub-lead and a fourth sub-lead, wherein each of the touch sensing electrodes has a first terminal electrically connected to a first terminal of a third sub-lead of a corresponding second lead, and a second terminal electrically connected to a first terminal of a fourth sub-lead of the corresponding second lead, a second terminal of the third sub-lead is electrically connected to a second terminal of the fourth sub-lead, and both the second terminal of the third sub-lead and the second terminal of the fourth sub-lead are electrically connected to a second wiring terminal in the binding area, and
a resistance of a part of the touch sensing electrode between a position where the touch sensing electrode is electrically connected to the corresponding fourth lead and a position where the touch sensing electrode is electrically connected to the third sub-lead is R5, a resistance of a part of the touch sensing electrode between a position where the touch sensing electrode is electrically connected to the corresponding fourth lead and a position where the touch sensing electrode is electrically connected to the fourth sub-lead is R6, a resistance of the third sub-lead is R7, a resistance of the fourth sub-lead is R8, and R5, R6, R7 and R8 satisfy $$2 \le \frac{R5+R7}{R6+R8} \le 9 \text{ or } 2 \le \frac{R6+R8}{R5+R7} \le 9.$$

2. The touch structure according to claim 1, wherein
the third leads are provided in a same layer as the touch driving electrodes, a third lead corresponding to one of the touch driving electrodes different from two outermost touch driving electrodes is located in a gap between the corresponding touch driving electrode and an adjacent touch driving electrode, and a third lead corresponding to one of the two outermost touch driving electrodes is located in a gap between the corresponding touch driving electrode and an adjacent touch driving electrode or is located on one side of the corresponding touch driving electrode away from the adjacent touch driving electrode; and
the fourth leads are provided in a same layer as the touch sensing electrodes, a fourth lead corresponding to one of the touch sensing electrodes different from two outermost touch sensing electrodes is located in a gap between the corresponding touch sensing electrode and an adjacent touch sensing electrode, and a fourth lead corresponding to one of the two outermost touch sensing electrodes is located in a gap between the corresponding touch sensing electrode and an adjacent touch sensing electrode or is located on one side of the corresponding touch sensing electrode away from the adjacent touch sensing electrode.

3. The touch structure according to claim 1, wherein R1, R2, R3 and R4 satisfy $$\frac{R1+R3}{R2+R4} = 2 \text{ or } \frac{R2+R4}{R1+R3} = 2;$$

and
R5, R6, R7 and R8 satisfy $$\frac{R5+R7}{R6+R8} = 2 \text{ or } \frac{R6+R8}{R5+R7} = 2.$$

4. The touch structure according to claim 1, wherein
each first lead has one terminal electrically connected to a corresponding touch driving electrode, and the other terminal electrically connected to a first wiring terminal in a binding area; and/or
each second lead has one terminal electrically connected to a corresponding touch sensing electrode, and the other terminal electrically connected to a second wiring terminal in the binding area.

5. The touch structure according to claim 4, wherein
each third lead is electrically connected to a terminal of a corresponding touch driving electrode which is not connected to the first lead; and
each fourth lead is electrically connected to a terminal of a corresponding touch sensing electrode which is not connected to the second lead.

6. The touch structure according to claim 1, further comprising an insulating layer located over the touch driving electrodes and the touch sensing electrodes, wherein
the insulating layer has via holes penetrating therethrough at positions corresponding to test points for the touch driving electrodes and/or test points for the touch sensing electrodes.

7. A touch panel, comprising a touch structure, the touch structure comprising:
a plurality of touch driving electrodes;
a plurality of touch sensing electrodes provided to intersect with the plurality of touch driving electrodes in an insulating manner;
a plurality of first leads insulated from each other and electrically connected to the touch driving electrodes in one-to-one correspondence;
a plurality of second leads insulated from each other and in one-to-one correspondence with the touch driving electrodes, wherein each third lead has one terminal electrically connected to a corresponding touch driving electrode and the other terminal serving as a test point for the touch driving electrode for testing whether there is an open circuit on the corresponding touch driving electrode and a corresponding first lead; and/or
a plurality of fourth leads insulated from each other and in one-to-one correspondence with the touch sensing electrodes, wherein each fourth lead has one terminal electrically connected to a corresponding touch sensing electrode and the other terminal serving as a test point for the touch sensing electrode for testing whether there is an open circuit on the corresponding touch sensing electrode and a corresponding second lead,
wherein
each first lead comprises a first sub-lead and a second sub-lead, wherein each touch driving electrode has one terminal electrically connected to one terminal of a first sub-lead of a corresponding first lead, and the other terminal electrically connected to one terminal of a second sub-lead of the corresponding first lead, the other terminal of the first sub-lead is electrically connected to the other terminal of the second sub-lead, and both the other terminal of the first sub-lead and the other terminal of the second sub-lead are electrically connected to a first wiring terminal in a binding area, a resistance of a part of the touch driving electrode between a position where the touch driving electrode is electrically connected to the corresponding third lead and a position where the touch driving electrode is electrically connected to the first sub-lead is R1, a resistance of a part of the touch driving electrode between a position where the touch driving electrode is electrically connected to the corresponding third lead and a position where the touch driving electrode is electrically connected to the second sub-lead is R2, a resistance of the first sub-lead is R3, a resistance of the second sub-lead is R4 and R1, R2, R3 and R4 satisfy $$2 \leq \frac{R1+R3}{R2+R4} \leq 9 \text{ or } 2 \leq \frac{R2+R4}{R1+R3} \leq 9;$$

and/or
each second lead comprises a third sub-lead and a fourth sub-lead, wherein each touch sensing electrode has one terminal electrically connected to one terminal of a third sub-lead of a corresponding second lead, and the other terminal electrically connected to one terminal of a fourth sub-lead of the corresponding second lead, the other terminal of the third sub-lead is electrically connected to the other terminal of the fourth sub-lead, and both the other terminal of the third sub-lead and the other terminal of the fourth sub-lead are electrically connected to a second wiring terminal in the binding area,
a resistance of a part of the touch sensing electrode between a position where the touch sensing electrode is electrically connected to the corresponding fourth lead and a position where the touch sensing electrode is electrically connected to the third sub-lead is R5, a resistance of a part of the touch sensing electrode between a position where the touch sensing electrode is electrically connected to the corresponding fourth lead and a position where the touch sensing electrode is electrically connected to the fourth sub-lead is, a resistance of the third sub-lead is, a resistance of the fourth sub-lead is R7 and R5, R6, R7, and R8 satisfy $$2 \leq \frac{R5+R7}{R6+R8} \leq 9 \text{ or } 2 \leq \frac{R6+R8}{R5+R7} \leq 9.$$

8. A display apparatus, comprising a touch panel that includes a touch structure, the touch structure comprising:
a plurality of touch driving electrodes;
a plurality of touch sensing electrodes provided to intersect with the plurality of touch driving electrodes in an insulating manner;
a plurality of first leads insulated from each other and electrically connected to the touch driving electrodes in one-to-one correspondence;
a plurality of second leads insulated from each other and electrically connected to the touch sensing electrodes in one-to-one correspondence;
a plurality of third leads insulated from each other and in one-to-one correspondence with the touch driving electrodes, wherein each third lead has one terminal electrically connected to a corresponding touch driving electrode and the other terminal serving as a test point for the touch driving electrode for testing whether there is an open circuit on the corresponding touch driving electrode and a corresponding first lead; and/or
a plurality of fourth leads insulated from each other and in one-to-one correspondence with the touch sensing electrodes, wherein each fourth lead has one terminal electrically connected to a corresponding touch sensing electrode and the other terminal serving as a test point for the touch sensing electrode for testing whether there is an open circuit on the corresponding touch sensing electrode and a corresponding second lead,
wherein
each first lead comprises a first sub-lead and a second sub-lead, wherein each touch driving electrode has one terminal electrically connected to one terminal of a first sub-lead of a corresponding first lead, and the other terminal electrically connected to one terminal of a second sub-lead of the corresponding first lead, the other terminal of the first sub-lead is electrically connected to the other terminal of the second sub-lead, and both the other terminal of the first sub-lead and the other terminal of the second sub-lead are electrically connected to a first wiring terminal in a binding area,
a resistance of a part of the touch driving electrode between a position where the touch driving electrode is electrically connected to the corresponding third lead and a position where the touch driving electrode is electrically connected to the first sub-lead is R1, a resistance of a part of the touch driving electrode between a position where the touch driving electrode is electrically connected to the corresponding third lead and a position where the touch driving electrode is electrically connected to the second sub-lead is R2, a resistance of the first sub-lead is R3, a resistance of the second sub-lead is R4, and R1, R2, R3 and R4 satisfy $$2 \leq \frac{R1+R3}{R2+R4} \leq 9 \text{ or } 2 \leq \frac{R2+R4}{R1+R3} \leq 9;$$

and/or
each second lead comprises a third sub-lead and a fourth sub-lead, wherein each touch sensing electrode has one terminal electrically connected to one terminal of a third sub-lead of a corresponding second lead, and the other terminal electrically connected to one terminal of a fourth sub-lead of the corresponding second lead, the other terminal of the third sub-lead is electrically connected to the other terminal of the fourth sub-lead, and both the other terminal of the third sub-lead and the other terminal of the fourth sub-lead are electrically connected to a second wiring terminal in the binding area,
a resistance of a part of the touch sensing electrode between a position where the touch sensing electrode is electrically connected to the corresponding fourth lead and a position where the touch sensing electrode is electrically connected to the third sub-lead is R5, a resistance of a part of the touch sensing electrode between a position where the touch sensing electrode is electrically connected to the corresponding fourth lead and a position where the touch sensing electrode is electrically connected to the fourth sub-lead is R6, a resistance of the third sub-lead is R7, a resistance of the fourth sub-lead is R8, and R5, R6, R7 and R8 satisfy $$2 \leq \frac{R5+R7}{R6+R8} \leq 9 \text{ or } 2 \leq \frac{R6+R8}{R5+R7} \leq 9.$$

9. A test method for the touch structure according to claim 1, comprising:
   measuring, for each touch driving electrode, a resistance between a test point for the touch driving electrode and a first wiring terminal to determine whether there is an open circuit on the touch driving electrode and a corresponding first lead; and
   measuring, for each touch sensing electrode, a resistance between a test point for the touch sensing electrode and a second wiring terminal to determine whether there is an open circuit on the touch sensing electrode and a corresponding second lead.

10. The test method according to claim 9, wherein determining whether there is an open circuit on the touch sensing electrode and a corresponding first lead comprises:
   when the measured resistance is R2+R4+R9, determining that there is an open circuit on a part of the touch driving electrode between a position where the touch driving electrode is electrically connected to the corresponding third lead and a position where the touch driving electrode is electrically connected to the first sub-lead and/or on the first sub-lead, wherein R9 is a resistance of the third lead;
   when the measured resistance is R1+R3+R9, determining that there is an open circuit on a part of the touch driving electrode between a position where the touch driving electrode is electrically connected to the corresponding third lead and a position where the touch driving electrode is electrically connected to the second sub-lead and/or on the second sub-lead, wherein R9 is the resistance of the third lead;
   when the measured resistance is abnormal, determining that there is an open circuit on the third lead corresponding to the touch driving electrode; and
   when the measured resistance is $$\frac{(R1+R3) \times (R2+R4)}{R1+R2+R3+R4} + R9,$$

determining that there is no open circuit on the touch driving electrode and the corresponding first lead, wherein R9 is the resistance of the third lead.

11. The test method according to claim 9, wherein determining whether there is an open circuit on the touch sensing electrode and a corresponding second lead comprises:
   when the measured resistance is R6+R8+R10, determining that there is an open circuit on a part of the touch sensing electrode between a position where the touch sensing electrode is electrically connected to the corresponding fourth lead and a position where the touch sensing electrode is electrically connected to the third sub-lead and/or on the third sub-lead, wherein R10 is a resistance of the fourth lead;
   when the measured resistance is R5+R7+R10, determining that there is an open circuit on a part of the touch sensing electrode between a position where the touch sensing electrode is electrically connected to the corresponding fourth lead and a position where the touch sensing electrode is electrically connected to the fourth sub-lead and/or on the fourth sub-lead, wherein R10 is the resistance of the fourth lead;
   when the measured resistance is abnormal, determining that there is an open circuit on the fourth lead corresponding to the touch sensing electrode; and
   when the measured resistance is $$\frac{(R5+R7) \times (R6+R8)}{R5+R6+R7+R8} + R10,$$

determining that there is no open circuit on the touch sensing electrode and the corresponding second lead, wherein R10 is the resistance of the fourth lead.

12. The test method according to claim 9, wherein determining whether there is an open circuit on the touch driving electrode and the corresponding first lead comprises:
   determining whether the measured resistance is abnormal;
   if the measured resistance is abnormal, determining that there is an open circuit on the touch driving electrode and/or the corresponding first lead and/or the corresponding third lead; and
   if the measured resistance is not abnormal, determining that there is no open circuit on the touch driving electrode and the corresponding first lead.

13. The test method according to claim 9, wherein determining whether there is an open circuit on the touch sensing electrode and the corresponding second lead comprises:
   determining whether the measured resistance is abnormal;
   if the measured resistance is abnormal, determining that there is an open circuit on the touch sensing electrode and/or the corresponding second lead and/or the corresponding fourth lead; and
   if the measured resistance is not abnormal, determining that there is no open circuit on the touch sensing electrode and the corresponding second lead.

14. The touch structure according to claim 3, further comprising an insulating layer located over the touch driving electrodes and the touch sensing electrodes, wherein
   the insulating layer has via holes penetrating therethrough at positions corresponding to test points for the touch driving electrodes and/or test points for the touch sensing electrodes.

15. The touch panel according to claim 7, wherein R1, R2, R3 and R4 satisfy $$\frac{R1+R3}{R2+R4} = 2 \text{ or } \frac{R2+R4}{R1+R3} = 2;$$

and
R5, R6, R7 and R8 satisfy $$\frac{R5+R7}{R6+R8} = 2 \text{ or } \frac{R6+R8}{R5+R7} = 2.$$

16. The touch panel according to claim 7, wherein the touch structure further comprises an insulating layer located over the touch driving electrodes and the touch sensing electrodes, wherein
   the insulating layer has via holes penetrating therethrough at positions corresponding to test points for the touch driving electrodes and/or test points for the touch sensing electrodes.

17. The display apparatus according to claim 8, wherein R1, R2, R3 and R4 satisfy $$\frac{R1+R3}{R2+R4}=2 \text{ or } \frac{R2+R4}{R1+R3}=2;$$

and
R5, R6, R7 and R8 satisfy $$\frac{R5+R7}{R6+R8}=2 \text{ or } \frac{R6+R8}{R5+R7}=2.$$

18. The display apparatus according to claim 8, wherein the touch structure further comprises an insulating layer located over the touch driving electrodes and the touch sensing electrodes, wherein
the insulating layer has via holes penetrating therethrough at positions corresponding to test points for the touch driving electrodes and/or test points for the touch sensing electrodes.

19. A test method for the touch structure according to claim 3, comprising:
measuring, for each touch driving electrode, a resistance between a test point for the touch driving electrode and a first wiring terminal to determine whether there is an open circuit on the touch driving electrode and a corresponding first lead; and
measuring, for each touch sensing electrode, a resistance between a test point for the touch sensing electrode and a second wiring terminal to determine whether there is an open circuit on the touch sensing electrode and a corresponding second lead.

20. A test method for the touch structure according to claim 6, comprising:
measuring, for each touch driving electrode, a resistance between a test point for the touch driving electrode and a first wiring terminal to determine whether there is an open circuit on the touch driving electrode and a corresponding first lead; and
measuring, for each touch sensing electrode, a resistance between a test point for the touch sensing electrode and a second wiring terminal to determine whether there is an open circuit on the touch sensing electrode and a corresponding second lead.

* * * * *